US012708361B2

(12) United States Patent
Evans et al.

(10) Patent No.: US 12,708,361 B2
(45) **Date of Patent: *Aug. 18, 2026**

(54) POWERED SURGICAL DEVICES INCLUDING PREDICTIVE MOTOR CONTROL

(71) Applicant: Covidien LP, Mansfield, MA (US)

(72) Inventors: Christopher Kelly Evans, Southington, CT (US); Thomas Wingardner, North Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/658,550

(22) Filed: May 8, 2024

(65) Prior Publication Data

US 2024/0341757 A1 Oct. 17, 2024

Related U.S. Application Data

(63) Continuation of application No. 17/987,619, filed on Nov. 15, 2022, now abandoned, which is a (Continued)

(51) Int. Cl.
*A61B 17/00* (2006.01)
*A61B 17/068* (2006.01)
(Continued)

(52) U.S. Cl.
CPC .......... *A61B 17/068* (2013.01); *A61B 17/115* (2013.01); *A61B 17/282* (2013.01);
(Continued)

(58) Field of Classification Search
CPC ... A61B 17/068; A61B 17/115; A61B 17/282; A61B 2017/00221; A61B 2017/00393;
(Continued)

(56) References Cited

U.S. PATENT DOCUMENTS 3,209,754 A 10/1965 Brown
3,273,562 A 9/1966 Brown
(Continued)

FOREIGN PATENT DOCUMENTS

CA 2733377 A1 * 9/2011 ............. A61B 34/76
CN 101683284 A 3/2010
(Continued)

OTHER PUBLICATIONS

European Search Report issued in corresponding European Application No. 19184928.0 dated Nov. 12, 2019, 7 pages.
(Continued)

*Primary Examiner* — Robert F Long

(57) ABSTRACT

A powered handheld electromechanical surgical device includes a motor configured to drive extension and retraction of a drive component, a sensor configured to sense force exerted on the drive component during extension of the drive component, and a controller including a processor and a non-transitory computer-readable storage medium storing instructions that, when executed by the processor, cause the processor to receive the sensed force from the sensor, control a speed of the motor during extension of the drive component in accordance with the sensed force, determine a speed profile or a force profile during extension of the drive component, and control a speed of the motor during retraction of the drive component in accordance with the speed profile or the force profile.

20 Claims, 5 Drawing Sheets

Related U.S. Application Data continuation of application No. 16/441,508, filed on Jun. 14, 2019, now Pat. No. 11,497,490.

(60) Provisional application No. 62/695,421, filed on Jul. 9, 2018.

(51) Int. Cl.
*A61B 17/115* (2006.01)
*A61B 17/28* (2006.01)
*A61B 17/072* (2006.01)

(52) U.S. Cl.
CPC ............... *A61B 2017/00221* (2013.01); *A61B 2017/00393* (2013.01); *A61B 2017/00398* (2013.01); *A61B 2017/00464* (2013.01); *A61B 2017/00473* (2013.01); *A61B 2017/00486* (2013.01); *A61B 2017/00734* (2013.01); *A61B 2017/07257* (2013.01); *A61B 2017/07271* (2013.01)

(58) Field of Classification Search
CPC .......... A61B 2017/00398; A61B 2017/00464; A61B 2017/00473; A61B 2017/00486; A61B 2017/00734; A61B 2017/07257; A61B 2017/07271; A61B 2017/00017; A61B 2017/0046; A61B 17/07207; A61B 17/072; A61B 90/06; A61B 2017/00137; A61B 2017/00367; A61B 2090/064
USPC ................................ 227/175.1–182.1, 8, 19
See application file for complete search history.

(56) References Cited

U.S. PATENT DOCUMENTS 3,499,591 A 3/1970 Green
3,528,693 A 9/1970 Pearson et al.
3,744,495 A 7/1973 Johnson
3,749,227 A * 7/1973 Denherder ............ A01K 43/00 198/383
3,862,631 A 1/1975 Austin
4,060,089 A 11/1977 Noiles
4,123,187 A * 10/1978 Turner .................... B23Q 5/12 408/137
4,204,623 A 5/1980 Green
4,217,902 A 8/1980 March
4,263,903 A 4/1981 Griggs
4,275,813 A 6/1981 Noiles
4,331,277 A 5/1982 Green
4,428,376 A 1/1984 Mericle
4,429,695 A 2/1984 Green
4,444,181 A 4/1984 Wevers et al.
4,454,875 A 6/1984 Pratt et al.
4,456,006 A 6/1984 Wevers et al.
4,485,816 A 12/1984 Krumme
4,485,817 A 12/1984 Swiggett
4,488,523 A 12/1984 Shichman
4,508,253 A 4/1985 Green
4,508,523 A 4/1985 Leu
4,522,206 A 6/1985 Whipple et al.
4,534,350 A 8/1985 Golden et al.
4,535,772 A 8/1985 Sheehan
4,566,620 A 1/1986 Green et al.
4,570,623 A 2/1986 Ellison et al.
4,606,343 A 8/1986 Conta et al.
4,606,344 A 8/1986 Di Giovanni
4,610,383 A 9/1986 Rothfuss et al.
4,612,923 A 9/1986 Kronenthal
4,612,933 A 9/1986 Brinkerhoff et al.
D286,442 S 10/1986 Korthoff et al.
4,627,437 A 12/1986 Bedi et al.
4,635,637 A 1/1987 Schreiber
4,662,371 A 5/1987 Whipple et al.
4,665,349 A * 5/1987 Matsuo ................ B60L 15/005 318/135
4,671,280 A 6/1987 Dorband et al.
4,705,038 A 11/1987 Sjostrom et al.
4,712,550 A 12/1987 Sinnett
4,719,917 A 1/1988 Barrows et al.
4,724,839 A 2/1988 Bedi et al.
4,731,058 A 3/1988 Doan
4,805,617 A 2/1989 Bedi et al.
4,807,628 A 2/1989 Peters et al.
4,852,558 A 8/1989 Outerbridge
4,913,144 A 4/1990 Del Medico
4,959,797 A * 9/1990 McIntosh .............. A63B 24/00 700/304
4,960,420 A 10/1990 Goble et al.
4,962,877 A 10/1990 Hervas
4,990,153 A 2/1991 Richards
4,994,073 A 2/1991 Green
4,995,877 A 2/1991 Ams et al.
5,040,715 A 8/1991 Green et al.
5,065,929 A 11/1991 Schulze et al.
5,089,009 A 2/1992 Green
5,108,422 A 4/1992 Green et al.
5,114,399 A 5/1992 Kovalcheck
5,129,570 A 7/1992 Schulze et al.
5,143,453 A 9/1992 Weynant nee Girones
5,203,864 A 4/1993 Phillips
5,207,697 A 5/1993 Carusillo et al.
5,209,756 A 5/1993 Seedhom et al.
5,246,443 A 9/1993 Mai
5,258,008 A 11/1993 Wilk
5,271,543 A 12/1993 Grant et al.
RE34,519 E 1/1994 Fox et al.
5,282,829 A 2/1994 Hermes
5,300,081 A 4/1994 Young et al.
5,307,976 A 5/1994 Olson et al.
5,312,023 A 5/1994 Green et al.
5,312,024 A 5/1994 Grant et al.
5,313,935 A 5/1994 Kortenbach et al.
5,318,221 A 6/1994 Green et al.
5,326,013 A 7/1994 Green et al.
5,330,486 A 7/1994 Wilk
5,332,142 A 7/1994 Robinson et al.
5,342,376 A 8/1994 Ruff
5,350,355 A 9/1994 Sklar
5,356,064 A 10/1994 Green et al.
5,359,993 A 11/1994 Slater et al.
5,364,001 A 11/1994 Bryan
5,381,943 A 1/1995 Allen et al.
5,383,874 A 1/1995 Jackson et al.
5,383,880 A 1/1995 Hooven
5,389,098 A 2/1995 Tsuruta et al.
5,391,166 A 2/1995 Eggers
5,395,030 A 3/1995 Kuramoto et al.
5,395,033 A 3/1995 Byrne et al.
5,400,267 A 3/1995 Denen et al.
5,403,312 A 4/1995 Yates et al.
5,405,344 A 4/1995 Williamson et al.
5,411,508 A 5/1995 Bessler et al.
5,413,267 A 5/1995 Solyntjes et al.
5,431,323 A 7/1995 Smith et al.
5,464,144 A 11/1995 Guy et al.
5,467,911 A 11/1995 Tsuruta et al.
5,478,344 A 12/1995 Stone et al.
5,482,100 A 1/1996 Kuhar
5,485,947 A 1/1996 Olson et al.
5,487,499 A 1/1996 Sorrentino et al.
5,497,933 A 3/1996 DeFonzo et al.
5,500,000 A 3/1996 Feagin et al.
5,503,320 A 4/1996 Webster et al.
5,507,743 A 4/1996 Edwards et al.
5,518,163 A 5/1996 Hooven
5,518,164 A 5/1996 Hooven
5,526,822 A 6/1996 Burbank et al.
5,529,235 A 6/1996 Burbank et al.
5,531,744 A 7/1996 Nardella et al.
5,533,661 A 7/1996 Main et al.
5,535,934 A 7/1996 Boiarski et al.
5,535,937 A 7/1996 Boiarski et al.

(56) References Cited

U.S. PATENT DOCUMENTS 5,558,671 A 9/1996 Yates
5,560,532 A 10/1996 DeFonzo et al.
5,562,239 A 10/1996 Boiarski et al.
5,571,285 A 11/1996 Chow et al.
5,575,799 A 11/1996 Bolanos et al.
5,582,611 A 12/1996 Tsuruta et al.
5,584,835 A 12/1996 Greenfield
5,601,224 A 2/1997 Bishop et al.
5,601,558 A 2/1997 Torrie et al.
5,607,095 A 3/1997 Smith et al.
5,609,285 A 3/1997 Grant et al.
5,609,560 A 3/1997 Ichikawa et al.
5,624,452 A 4/1997 Yates
5,632,433 A 5/1997 Grant et al.
5,634,926 A 6/1997 Jobe
5,642,848 A 7/1997 Ludwig et al.
5,653,374 A 8/1997 Young et al.
5,658,300 A 8/1997 Bito et al.
5,658,312 A 8/1997 Green et al.
5,662,662 A 9/1997 Bishop et al.
5,665,085 A 9/1997 Nardella
5,667,513 A 9/1997 Torrie et al.
5,667,517 A 9/1997 Hooven
5,667,527 A 9/1997 Cook
5,669,544 A 9/1997 Schulze et al.
5,673,841 A 10/1997 Schulze et al.
5,676,674 A 10/1997 Bolanos et al.
5,680,981 A 10/1997 Milili et al.
5,680,982 A 10/1997 Schulze et al.
5,690,675 A 11/1997 Sawyer et al.
5,692,668 A 12/1997 Schulze et al.
5,695,506 A 12/1997 Pike et al.
5,695,524 A 12/1997 Kelley et al.
5,702,447 A 12/1997 Walch et al.
5,704,534 A 1/1998 Huitema et al.
5,713,505 A 2/1998 Huitema
5,713,896 A 2/1998 Nardella
5,715,987 A 2/1998 Kelley et al.
5,716,366 A 2/1998 Yates
5,720,753 A 2/1998 Sander et al.
5,725,529 A 3/1998 Nicholson et al.
5,728,110 A 3/1998 Vidal et al.
5,728,116 A 3/1998 Rosenman
5,730,757 A 3/1998 Benelli et al.
5,735,848 A 4/1998 Yates et al.
5,738,474 A 4/1998 Blewett
5,755,726 A 5/1998 Pratt et al.
5,759,171 A 6/1998 Coelho et al.
5,779,130 A 7/1998 Alesi et al.
5,782,397 A 7/1998 Koukline
5,785,713 A 7/1998 Jobe
5,788,698 A 8/1998 Savornin
5,810,811 A 9/1998 Yates et al.
5,823,066 A 10/1998 Huitema et al.
5,829,662 A 11/1998 Allen et al.
5,830,121 A 11/1998 Enomoto et al.
5,849,023 A 12/1998 Mericle
5,849,028 A 12/1998 Chen
5,855,311 A 1/1999 Hamblin et al.
5,861,005 A 1/1999 Kontos
5,865,361 A 2/1999 Milliman et al.
5,876,401 A 3/1999 Schulze et al.
5,891,156 A 4/1999 Gessner et al.
5,893,813 A 4/1999 Yamamoto
5,895,396 A 4/1999 Day et al.
5,906,607 A 5/1999 Taylor et al.
5,911,721 A 6/1999 Nicholson et al.
5,918,791 A 7/1999 Sorrentino et al.
5,928,222 A 7/1999 Kleinerrnan
5,944,717 A 8/1999 Lee et al.
5,944,736 A 8/1999 Taylor et al.
5,954,259 A 9/1999 Viola et al.
5,961,521 A 10/1999 Roger
5,964,394 A 10/1999 Robertson
5,968,044 A 10/1999 Nicholson et al.
5,976,171 A 11/1999 Taylor
5,980,518 A 11/1999 Carr et al.
5,980,548 A 11/1999 Evans et al.
5,991,355 A 11/1999 Dahlke
5,991,650 A 11/1999 Swanson et al.
5,992,724 A 11/1999 Snyder
5,997,552 A 12/1999 Person et al.
6,004,335 A 12/1999 Vaitekunas et al.
6,007,550 A 12/1999 Wang et al.
6,010,054 A 1/2000 Johnson et al.
6,013,077 A 1/2000 Harwin
6,015,417 A 1/2000 Reynolds, Jr.
6,017,354 A 1/2000 Culp et al.
6,030,410 A 2/2000 Zurbrugg
6,032,849 A 3/2000 Mastri et al.
6,039,731 A 3/2000 Taylor et al.
6,051,007 A 4/2000 Hogendijk et al.
6,063,078 A 5/2000 Wittkampf
6,063,095 A 5/2000 Wang et al.
6,077,246 A 6/2000 Kullas et al.
6,079,606 A 6/2000 Milliman et al.
6,080,150 A 6/2000 Gough
6,083,242 A 7/2000 Cook
6,090,123 A 7/2000 Culp et al.
6,092,422 A 7/2000 Binnig et al.
6,109,500 A 8/2000 Alli et al.
6,113,592 A 9/2000 Taylor
6,123,702 A 9/2000 Swanson et al.
6,126,058 A 10/2000 Adams et al.
6,126,651 A 10/2000 Mayer
6,127,811 A 10/2000 Shenoy et al.
6,132,425 A 10/2000 Gough
6,165,169 A 12/2000 Panescu et al.
6,166,538 A 12/2000 D'Alfonso
6,179,840 B1 1/2001 Bowman
6,187,009 B1 2/2001 Herzog et al.
6,187,019 B1 2/2001 Stefanchik et al.
6,190,401 B1 2/2001 Green et al.
6,193,501 B1 2/2001 Masel et al.
6,202,914 B1 3/2001 Geiste et al.
6,217,573 B1 4/2001 Webster
6,228,534 B1 5/2001 Takeuchi et al.
6,231,565 B1 5/2001 Tovey et al.
6,236,874 B1 5/2001 Devlin et al.
6,237,604 B1 5/2001 Burnside et al.
6,241,139 B1 6/2001 Milliman et al.
6,245,065 B1 6/2001 Panescu et al.
6,248,117 B1 6/2001 Blatter
6,250,532 B1 6/2001 Green et al.
6,258,111 B1 7/2001 Ross et al.
6,264,086 B1 7/2001 McGuckin, Jr.
6,264,087 B1 7/2001 Whitman
6,264,653 B1 7/2001 Falwell
6,281,471 B1 8/2001 Smart
6,288,534 B1 9/2001 Starkweather et al.
6,290,701 B1 9/2001 Enayati
6,293,943 B1 9/2001 Panescu et al.
6,295,330 B1 9/2001 Skog et al.
6,315,184 B1 11/2001 Whitman
6,329,778 B1 12/2001 Culp et al.
6,330,965 B1 12/2001 Milliman et al.
6,346,104 B2 2/2002 Daly et al.
6,355,066 B1 3/2002 Kim
6,364,884 B1 4/2002 Bowman et al.
6,387,092 B1 5/2002 Burnside et al.
6,388,240 B2 5/2002 Schulz et al.
6,402,766 B2 6/2002 Bowman et al.
6,412,279 B1 7/2002 Coleman et al.
6,425,903 B1 7/2002 Voegele
6,436,097 B1 8/2002 Nardella
6,436,107 B1 8/2002 Wang et al.
6,436,110 B2 8/2002 Bowman et al.
6,443,973 B1 9/2002 Whitman
6,447,517 B1 9/2002 Bowman
6,461,372 B1 10/2002 Jensen et al.
6,478,210 B2 11/2002 Adams et al.
6,497,707 B1 12/2002 Bowman et al.
6,505,768 B2 1/2003 Whitman
6,515,273 B2 2/2003 Al-Ali

(56) References Cited

U.S. PATENT DOCUMENTS 6,524,316 B1 2/2003 Nicholson et al.
6,533,157 B1 3/2003 Whitman
6,540,751 B2 4/2003 Enayati
6,544,273 B1 4/2003 Harari et al.
6,554,852 B1 4/2003 Olberlander
6,562,071 B2 5/2003 Jarvinen
6,578,579 B2 6/2003 Burnside et al.
6,601,748 B1 8/2003 Fung et al.
6,601,749 B2 8/2003 Sullivan et al.
6,602,252 B2 8/2003 Mollenauer
6,611,793 B1 8/2003 Burnside et al.
6,616,821 B2 9/2003 Broadley et al.
6,629,986 B1 10/2003 Ross et al.
6,651,669 B1 11/2003 Burnside
6,656,177 B2 12/2003 Truckai et al.
6,669,073 B2 12/2003 Milliman et al.
6,669,705 B2 12/2003 Westhaver et al.
6,696,008 B2 2/2004 Brandinger
6,698,643 B2 3/2004 Whitman
6,699,177 B1 3/2004 Wang et al.
6,716,233 B1 4/2004 Whitman
6,736,085 B1 5/2004 Esnouf
6,792,390 B1 9/2004 Burnside et al.
6,793,652 B1 9/2004 Whitman et al.
6,817,508 B1 11/2004 Racenet et al.
6,830,174 B2 12/2004 Hillstead et al.
6,843,403 B2 1/2005 Whitman
6,846,307 B2 1/2005 Whitman et al.
6,846,308 B2 1/2005 Whitman et al.
6,846,309 B2 1/2005 Whitman et al.
6,849,071 B2 2/2005 Whitman et al.
6,861,639 B2 3/2005 Al-Ali
6,872,214 B2 3/2005 Sonnenschein et al.
6,899,538 B2 5/2005 Matoba
6,900,004 B2 5/2005 Satake
6,905,057 B2 6/2005 Swayze et al.
6,926,636 B2 8/2005 Luper
6,953,139 B2 10/2005 Milliman et al.
6,959,852 B2 11/2005 Shelton, IV et al.
6,964,363 B2 11/2005 Wales et al.
6,979,328 B2 12/2005 Baerveldt et al.
6,981,628 B2 1/2006 Wales
6,981,941 B2 1/2006 Whitman et al.
6,988,649 B2 1/2006 Shelton, IV et al.
7,000,819 B2 2/2006 Swayze et al.
7,032,798 B2 4/2006 Whitman et al.
7,044,353 B2 5/2006 Mastri et al.
7,048,687 B1 5/2006 Reuss et al.
7,055,731 B2 6/2006 Shelton, IV et al.
7,059,508 B2 6/2006 Shelton, IV et al.
7,077,856 B2 7/2006 Whitman
7,083,075 B2 8/2006 Swayze et al.
7,097,089 B2 8/2006 Marczyk
7,111,769 B2 9/2006 Wales et al.
7,118,564 B2 10/2006 Ritchie et al.
7,122,029 B2 10/2006 Koop et al.
7,128,253 B2 10/2006 Mastri et al.
7,128,254 B2 10/2006 Shelton, IV et al.
7,140,528 B2 11/2006 Shelton, IV
7,143,924 B2 12/2006 Scirica et al.
7,143,925 B2 12/2006 Shelton, IV et al.
7,143,926 B2 12/2006 Shelton, IV et al.
7,147,138 B2 12/2006 Shelton, IV
7,186,966 B2 3/2007 Al-Ali
7,193,519 B2 3/2007 Root et al.
7,217,269 B2 5/2007 El-Galley et al.
7,220,232 B2 5/2007 Suorsa et al.
7,240,817 B2 7/2007 Higuchi
7,241,270 B2 7/2007 Horzewski et al.
7,246,734 B2 7/2007 Shelton, IV
7,303,108 B2 12/2007 Shelton, IV
7,328,828 B2 2/2008 Ortiz et al.
7,335,169 B2 2/2008 Thompson et al.
7,364,061 B2 4/2008 Swayze et al.
7,380,695 B2 6/2008 Doll et al.
7,380,696 B2 6/2008 Shelton, IV et al.
7,404,508 B2 7/2008 Smith et al.
7,416,101 B2 8/2008 Shelton, IV et al.
7,419,080 B2 9/2008 Smith et al.
7,422,136 B1 9/2008 Marczyk
7,422,139 B2 9/2008 Shelton, IV et al.
7,431,188 B1 10/2008 Marczyk
7,431,189 B2 10/2008 Shelton, IV et al.
7,434,715 B2 10/2008 Shelton, IV et al.
7,441,684 B2 10/2008 Shelton, IV et al.
7,461,767 B2 12/2008 Viola et al.
7,464,846 B2 12/2008 Shelton, IV et al.
7,464,847 B2 12/2008 Viola et al.
7,464,849 B2 12/2008 Shelton, IV et al.
7,481,348 B2 1/2009 Marczyk
7,487,899 B2 2/2009 Shelton, IV et al.
7,549,563 B2 6/2009 Mather et al.
7,552,854 B2 6/2009 Wixey et al.
7,556,185 B2 7/2009 Viola
7,568,603 B2 8/2009 Shelton, IV et al.
7,637,409 B2 12/2009 Marczyk
7,641,093 B2 1/2010 Doll et al.
7,644,848 B2 1/2010 Swayze et al.
7,648,055 B2 1/2010 Marczyk
7,670,334 B2 3/2010 Hueil et al.
7,694,809 B2 4/2010 Garbini et al.
7,721,931 B2 5/2010 Shelton, IV et al.
7,740,159 B2 6/2010 Shelton, IV et al.
7,753,248 B2 7/2010 Viola
7,757,925 B2 7/2010 Viola et al.
7,766,207 B2 8/2010 Mather et al.
7,766,210 B2 8/2010 Shelton, IV et al.
7,770,775 B2 8/2010 Shelton, IV et al.
7,784,663 B2 8/2010 Shelton, IV
7,815,090 B2 10/2010 Marczyk
7,819,896 B2 10/2010 Racenet
7,823,760 B2 11/2010 Zemlok et al.
7,845,534 B2 12/2010 Viola et al.
7,870,989 B2 1/2011 Viola et al.
7,886,953 B2 2/2011 Schwemberger et al.
7,887,530 B2 2/2011 Zemlok et al.
7,905,897 B2 3/2011 Whitman et al.
7,909,221 B2 3/2011 Viola et al.
7,922,063 B2 4/2011 Zemlok et al.
7,931,660 B2 4/2011 Aranyi et al.
7,950,560 B2 5/2011 Zemlok et al.
7,955,352 B2 6/2011 McEwen et al.
8,006,885 B2 8/2011 Marczyk
8,006,887 B2 8/2011 Marczyk
8,011,551 B2 9/2011 Marczyk et al.
8,020,742 B2 9/2011 Marczyk
8,025,199 B2 9/2011 Whitman et al.
8,038,044 B2 10/2011 Viola
8,052,024 B2 11/2011 Viola et al.
8,066,721 B2 11/2011 Kortenbach et al.
8,074,858 B2 12/2011 Marczyk
8,092,493 B2 1/2012 Marczyk
8,128,645 B2 3/2012 Sonnenschein et al.
8,132,705 B2 3/2012 Viola et al.
8,157,150 B2 4/2012 Viola et al.
8,186,555 B2 5/2012 Shelton, IV et al.
8,201,721 B2 6/2012 Zemlok et al.
8,210,412 B2 7/2012 Marczyk
8,240,536 B2 8/2012 Marczyk
8,240,537 B2 8/2012 Marczyk
8,267,924 B2 9/2012 Zemlok et al.
8,328,823 B2 12/2012 Aranyi et al.
8,348,125 B2 1/2013 Viola et al.
8,685,004 B2 4/2014 Zemlock et al.
9,192,381 B2 11/2015 Marczyk
9,364,222 B2 6/2016 Zemlok et al.
9,370,360 B2 6/2016 Marczyk
9,370,361 B2 6/2016 Viola et al.
9,433,415 B2 9/2016 Marczyk et al.
9,480,492 B2 11/2016 Aranyi et al.
9,585,659 B2 3/2017 Viola et al.
9,764,357 B2 9/2017 Houston
11,497,490 B2 11/2022 Evans et al.
11,504,126 B2 * 11/2022 Shelton, IV ....... A61B 17/1285

(56) References Cited

U.S. PATENT DOCUMENTS 11,576,668 B2* 2/2023 Shelton, IV ......... A61B 17/068
2002/0103489 A1 8/2002 Ku
2002/0111641 A1 8/2002 Peterson et al.
2002/0143350 A1* 10/2002 Heitzmann .... A61B 17/320758 606/159
2002/0165541 A1 11/2002 Whitman
2003/0090201 A1 5/2003 Peng
2003/0114851 A1 6/2003 Truckai et al.
2003/0120306 A1 6/2003 Burbank et al.
2003/0178465 A1 9/2003 Bilotti
2003/0230655 A1* 12/2003 Giberson ................ F16D 33/16 241/101.2
2004/0049219 A1 3/2004 Briggs
2004/0122292 A1 6/2004 Dey
2004/0232201 A1 11/2004 Wenchell et al.
2005/0006429 A1 1/2005 Wales et al.
2005/0010235 A1 1/2005 VanDusseldorp
2005/0090740 A1 4/2005 Raitzer
2005/0116673 A1 6/2005 Carl et al.
2005/0131390 A1 6/2005 Heinrich et al.
2005/0139636 A1 6/2005 Schwemberger et al.
2005/0177176 A1 8/2005 Gerbi et al.
2005/0192609 A1 9/2005 Whitman et al.
2005/0247753 A1 11/2005 Kelly et al.
2006/0000867 A1 1/2006 Shelton et al.
2006/0151567 A1 7/2006 Roy
2006/0151568 A1 7/2006 Weller
2006/0156876 A1 7/2006 Sussmeier
2007/0023477 A1 2/2007 Whitman et al.
2007/0029363 A1 2/2007 Popov
2007/0084897 A1 4/2007 Shelton et al.
2007/0102472 A1 5/2007 Shelton
2007/0175949 A1 8/2007 Shelton et al.
2007/0175950 A1 8/2007 Shelton et al.
2007/0175951 A1 8/2007 Shelton et al.
2007/0175955 A1 8/2007 Shelton et al.
2007/0219563 A1 9/2007 Voegele
2007/0270790 A1 11/2007 Smith et al.
2008/0021490 A1* 1/2008 Briggs ............... A61B 5/15113 606/181
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0041918 A1 2/2008 Holsten
2008/0135600 A1 6/2008 Hiranuma et al.
2008/0169329 A1 7/2008 Shelton et al.
2008/0185419 A1 8/2008 Smith et al.
2008/0197167 A1 8/2008 Viola et al.
2008/0255413 A1 10/2008 Zemlok et al.
2008/0255607 A1 10/2008 Zemlok
2008/0262476 A1* 10/2008 Krause ............. A61B 17/32002 606/34
2009/0012556 A1 1/2009 Boudreaux et al.
2009/0018624 A1 1/2009 Levinson et al.
2009/0024142 A1 1/2009 Ruiz Morales
2009/0054909 A1 2/2009 Farritor et al.
2009/0065258 A1 3/2009 Hamilton
2009/0090201 A1 4/2009 Viola
2009/0090763 A1 4/2009 Zemlok et al.
2009/0108048 A1 4/2009 Zemlok et al.
2009/0270896 A1 10/2009 Sullivan
2010/0001036 A1 1/2010 Marczyk et al.
2010/0163023 A1 7/2010 Singh
2010/0200636 A1 8/2010 Zemlok et al.
2010/0251832 A1* 10/2010 Kirkpatrick ....... G01M 17/0074 73/862.191
2010/0270355 A1 10/2010 Whitman et al.
2010/0312257 A1 12/2010 Aranyi
2010/0320254 A1 12/2010 Zemlok et al.
2011/0022032 A1 1/2011 Zemlok et al.
2011/0034910 A1 2/2011 Ross et al.
2011/0062211 A1 3/2011 Ross et al.
2011/0125138 A1 5/2011 Malinouskas et al.
2011/0139851 A1 6/2011 Mc Cuen
2011/0146922 A1 6/2011 Colson
2011/0168757 A1 7/2011 Viola et al.
2011/0172681 A1 7/2011 Aranyi et al.
2011/0176849 A1 7/2011 Abe
2011/0190738 A1 8/2011 Zemlok et al.
2011/0301579 A1 12/2011 Marczyk et al.
2011/0303735 A1 12/2011 Marczyk
2012/0037686 A1 2/2012 Hessler
2012/0055972 A1 3/2012 Marczyk
2012/0071895 A1* 3/2012 Stahler .................. A61B 34/35 606/130
2012/0074197 A1 3/2012 Marczyk
2012/0076666 A1* 3/2012 Romain .................... F04B 5/02 417/42
2012/0116379 A1* 5/2012 Yates .................. A61B 17/295 606/33
2012/0175400 A1 7/2012 Viola et al.
2012/0180438 A1* 7/2012 Lagares Corominas .................... B26D 7/32 83/102
2012/0186369 A1* 7/2012 Matlschweiger . G01M 17/0078 73/865.3
2012/0193393 A1 8/2012 Viola et al.
2012/0198288 A1 8/2012 Njo et al.
2012/0220989 A1 8/2012 Zemlok et al.
2012/0223121 A1 9/2012 Viola et al.
2012/0241494 A1 9/2012 Marczyk
2012/0248167 A1 10/2012 Flanagan et al.
2012/0277790 A1 11/2012 Zemlok et al.
2012/0298718 A1 11/2012 Marczyk
2012/0298720 A1 11/2012 Marczyk
2013/0018400 A1 1/2013 Milton et al.
2013/0116668 A1* 5/2013 Shelton, IV .......... A61B 34/74 606/1
2013/0214025 A1 8/2013 Zemlok
2013/0321262 A1 12/2013 Schecter
2013/0324999 A1* 12/2013 Price ............. A61B 17/320068 606/1
2014/0012289 A1 1/2014 Snow et al.
2014/0081176 A1 3/2014 Hassan
2014/0142507 A1 5/2014 Armes
2014/0148808 A1 5/2014 Inkpen
2014/0166323 A1 6/2014 Cooper
2014/0171923 A1 6/2014 Aranyi
2014/0194250 A1 7/2014 Reich
2014/0239037 A1 8/2014 Boudreaux
2014/0263538 A1 9/2014 Leimbach
2014/0288792 A1* 9/2014 Somoza ................. F16H 61/66 701/58
2014/0291382 A1 10/2014 Lloyd
2015/0053749 A1 2/2015 Shelton, IV et al.
2015/0054753 A1 2/2015 Morgan et al.
2015/0080912 A1 3/2015 Sapre
2015/0122870 A1* 5/2015 Zemlok ........... A61B 17/07207 227/176.1
2015/0182221 A1* 7/2015 McCuen .......... A61B 17/07207 227/175.1
2015/0209059 A1 7/2015 Trees
2015/0272575 A1 10/2015 Leimbach et al.
2015/0282822 A1* 10/2015 Trees ................ A61B 18/1445 606/41
2015/0351765 A1* 12/2015 Valentine ............ G06F 11/1464 227/176.1
2015/0374449 A1 12/2015 Chowaniec et al.
2016/0128704 A1 5/2016 McGinley
2016/0157926 A1* 6/2016 Boudreaux .......... A61B 17/295 606/170
2016/0174977 A1* 6/2016 Lytle, IV ............ A61B 17/068 227/180.1
2016/0242779 A1 8/2016 Aranyi et al.
2016/0278872 A1 9/2016 Gombert
2016/0310134 A1 10/2016 Contini et al.
2017/0079640 A1 3/2017 Overmyer
2017/0095897 A1 4/2017 Moraru
2017/0105614 A1 4/2017 McWilliam
2017/0202591 A1 7/2017 Shelton, IV
2017/0202605 A1 7/2017 Shelton, IV

(56) References Cited

U.S. PATENT DOCUMENTS

| | | | |
|---|---|---|---|
| 2017/0202607 | A1 | 7/2017 | Shelton, IV et al. |
| 2017/0215720 | A1 | 8/2017 | Walker |
| 2017/0245854 | A1 | 8/2017 | Zemlok et al. |
| 2017/0249431 | A1 | 8/2017 | Shelton, IV |
| 2017/0281187 | A1 | 10/2017 | Shelton, IV |
| 2017/0296179 | A1 | 10/2017 | Shelton, IV |
| 2017/0296213 | A1* | 10/2017 | Swensgard ........... A61B 17/32 |
| 2018/0132850 | A1 | 5/2018 | Leimbach |
| 2018/0250002 | A1 | 9/2018 | Eschbach |
| 2018/0250004 | A1 | 9/2018 | Williams |
| 2018/0318133 | A1 | 11/2018 | Clauson et al. |
| 2018/0321119 | A1* | 11/2018 | Yin .......................... G01N 3/56 |
| 2018/0345972 | A1 | 12/2018 | Turkoglu |
| 2018/0360449 | A1* | 12/2018 | Shelton, IV ....... A61B 17/0686 |
| 2018/0360450 | A1* | 12/2018 | Shelton, IV ......... A61B 17/072 |
| 2018/0360452 | A1* | 12/2018 | Shelton, IV ......... A61B 17/068 |
| 2018/0360473 | A1* | 12/2018 | Shelton, IV ........... A61B 34/76 |
| 2019/0038371 | A1* | 2/2019 | Wixey ............. A61B 17/07207 |
| 2019/0133577 | A1 | 5/2019 | Weadock |
| 2019/0150925 | A1 | 5/2019 | Marczyk |
| 2019/0161904 | A1* | 5/2019 | Nam ....................... D06F 39/14 |
| 2019/0183494 | A1 | 6/2019 | Shelton, IV |
| 2019/0183503 | A1 | 6/2019 | Shelton, IV |
| 2019/0201034 | A1 | 7/2019 | Shelton, IV et al. |
| 2019/0261984 | A1 | 8/2019 | Nelson |
| 2020/0107898 | A1 | 4/2020 | Kim |
| 2020/0113584 | A1* | 4/2020 | McGinley .......... A61B 17/1622 |
| 2020/0360041 | A1 | 11/2020 | Marinkovic |
| 2020/0375447 | A1 | 12/2020 | Kotamarti |
| 2021/0000563 | A1* | 1/2021 | Evans .............. A61B 17/07207 |
| 2021/0132589 | A1* | 5/2021 | Takeuchi ........... G05B 19/4155 |
| 2022/0227604 | A1* | 7/2022 | Chen ..................... B66C 13/063 |
| 2023/0041810 | A1 | 2/2023 | Thompson |
| 2023/0051271 | A1* | 2/2023 | Shelton, IV ..... A61B 17/07207 |
| 2023/0070423 | A1 | 3/2023 | Evans |

FOREIGN PATENT DOCUMENTS

| | | | | |
|---|---|---|---|---|
| CN | 102648864 | A | 8/2012 | |
| EP | 0537570 | A2 | 4/1993 | |
| EP | 0647431 | A2 | 4/1995 | |
| EP | 0738501 | A1 | 10/1996 | |
| EP | 0770354 | A1 | 5/1997 | |
| EP | 1070487 | A2 | 1/2001 | |
| EP | 1201196 | A1 | 5/2002 | |
| EP | 1658817 | A1 | 5/2006 | |
| EP | 1813203 | A2 | 8/2007 | |
| EP | 2954854 | A2 | 12/2015 | |
| EP | 3231373 | A2 | 10/2017 | |
| FR | 2849589 | A1 | 7/2004 | |
| JP | 2010253272 | A | 11/2010 | |
| JP | 2020524046 | A | 8/2020 | |
| JP | 7139366 | B2 * | 9/2022 | ....... A61B 17/07207 |
| WO | 9414129 | A1 | 6/1994 | |
| WO | 9729694 | A1 | 8/1997 | |
| WO | 9740760 | A1 | 11/1997 | |
| WO | 9837825 | A1 | 9/1998 | |
| WO | 9952489 | A1 | 10/1999 | |
| WO | 0234140 | A2 | 5/2002 | |
| WO | 03026511 | A1 | 4/2003 | |
| WO | 03030743 | A2 | 4/2003 | |
| WO | 2004032760 | A2 | 4/2004 | |
| WO | 2007030753 | A2 | 3/2007 | |
| WO | 2007114868 | A2 | 10/2007 | |
| WO | 2007118179 | A2 | 10/2007 | |
| WO | 2007014355 | A3 | 4/2009 | |
| WO | 2009143092 | A1 | 11/2009 | |
| WO | 2016036811 | Z1 | 3/2016 | |
| WO | 2017180428 | A1 | 10/2017 | |

OTHER PUBLICATIONS

Japanese Office Action issued in corresponding Japanese Application No. 2019-123487 mailed Jun. 1, 2023, 6 pages.

* cited by examiner

POWERED SURGICAL DEVICES INCLUDING PREDICTIVE MOTOR CONTROL

CROSS-REFERENCE TO RELATED APPLICATIONS

This application is a continuation application of U.S. patent application Ser. No. 17/987,619 filed on Nov. 15, 2022 which is a continuation of U.S. patent application Ser. No. 16/441,508, filed on Jun. 14, 2019, now U.S. Pat. No. 11,497,490, which claims the benefit of and priority to U.S. Provisional Patent Application Ser. No. 62/695,421, filed on Jul. 9, 2018, the entire contents of each of which being incorporated by reference herein.

TECHNICAL FIELD

The present disclosure relates generally to surgical devices. More particularly, the present disclosure relates to powered handheld electromechanical surgical devices.

BACKGROUND

A number of manufacturers have developed surgical devices incorporating powered drive systems for operating and/or manipulating an end effector at a distal end of the device. In many instances, the surgical devices include a powered handle assembly that is reusable and a end effector that is selectively connected to the powered handle assembly prior to use and then disconnected therefrom following use in order to be disposed of or, in some instances, sterilized for re-use.

The use of powered surgical devices such as, for example, electromechanical surgical staplers, has grown tremendously over the past few decades. Advanced technologies and informatics within these intelligent devices provide the ability to gather clinical and operational data that can be used to improve performance, drive design improvements and, ultimately, improve patient outcomes.

SUMMARY

As detailed herein and shown in the drawing figures, as is traditional when referring to relative positioning on a surgical instrument, the term "proximal" refers to the end of the apparatus or component thereof which is closer to the user and the term "distal" refers to the end of the apparatus or component thereof which is further away from the user. Further, to the extent consistent, any or all of the aspects and features detailed herein may be used in conjunction with any or all of the other aspects and features detailed herein.

Provided in accordance with aspects of the present disclosure is a powered handheld electromechanical surgical device including a motor configured to drive extension and retraction of a drive component, a sensor configured to sense force exerted on the drive component during extension of the drive component, and a controller including a processor and a non-transitory computer-readable storage medium. The storage medium stores instructions that, when executed by the processor, cause the processor to receive the sensed force from the sensor, control a speed of the motor during extension of the drive component in accordance with the sensed force, determine a speed profile and/or a force profile during extension of the drive component, and control a speed of the motor during retraction of the drive component in accordance with the speed profile and/or the force profile.

In an aspect of the present disclosure, the powered handheld electromechanical surgical device according further includes a handle assembly including the motor and controller disposed therein, and an adapter assembly releasably engaged with the handle assembly and including the drive component and sensor disposed therein.

In another aspect of the present disclosure, the powered handheld electromechanical surgical device further includes an end effector releasably engaged with the adapter assembly. In such aspects, extension of the drive component at least one of closes or fires the end effector and retraction of the drive component opens the end effector.

In yet another aspect of the present disclosure, the sensor is a strain gauge.

In still another aspect of the present disclosure, the motor provides a rotational output. The rotational output is converted into translation of the drive component to extend and retract the drive component.

A method of controlling a powered handheld electromechanical surgical device provided in accordance with aspects of the present disclosure includes activating a motor to drive extension of a drive component, sensing force exerted on the drive component during extension of the drive component, controlling a speed of the motor during extension of the drive component in accordance with the sensed force, determining one of speed profile during extension of the drive component or a force profile during extension of the drive component, and controlling a speed of the motor during retraction of the drive component in accordance with the speed profile or the force profile.

BRIEF DESCRIPTION OF THE DRAWINGS

Aspects and features of the present disclosure are described in detail with reference to the drawing figures wherein like reference numerals identify similar or identical structural elements and.

DETAILED DESCRIPTION

Figure 1:
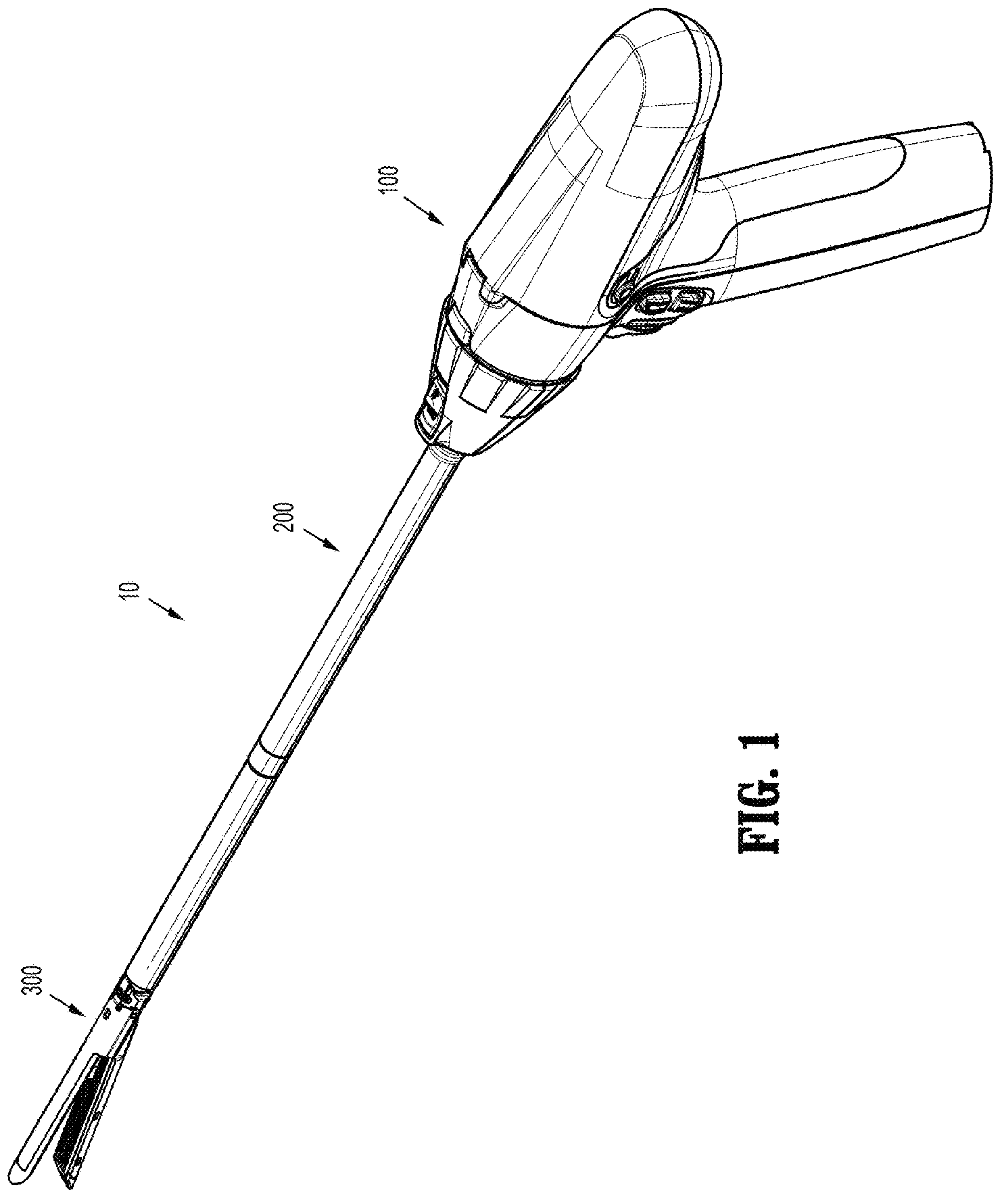
FIG. 1 is a perspective view of a surgical device configured for use in accordance with the present disclosure and including a handle assembly, an adapter assembly, and an end effector.

Turning to FIG. 1, a powered handheld electromechanical surgical device exemplifying the aspects and features of the present disclosure is shown generally identified by reference numeral 10. Surgical device 10 includes a handle assembly 100, an adapter assembly 200, and an end effector 300. Handle assembly 100 is configured for selective connection with adapter assembly 200 and, in turn, adapter assembly 200 is configured for selective connection with end effector 300. Although detailed herein with respect to surgical device 10, it is understood that the aspects and features of the present disclosure apply equally to any suitable powered handheld electromechanical surgical device. Thus, surgical device 10 is detailed herein only to the extent necessary to exemplify the aspects and features of the present disclosure. A more detailed description of surgical device 10 can be found in commonly owned U.S. Patent Appl. Pub. No. 2016/0310134, the entire contents of which are hereby incorporated herein by reference.

Figure 2:
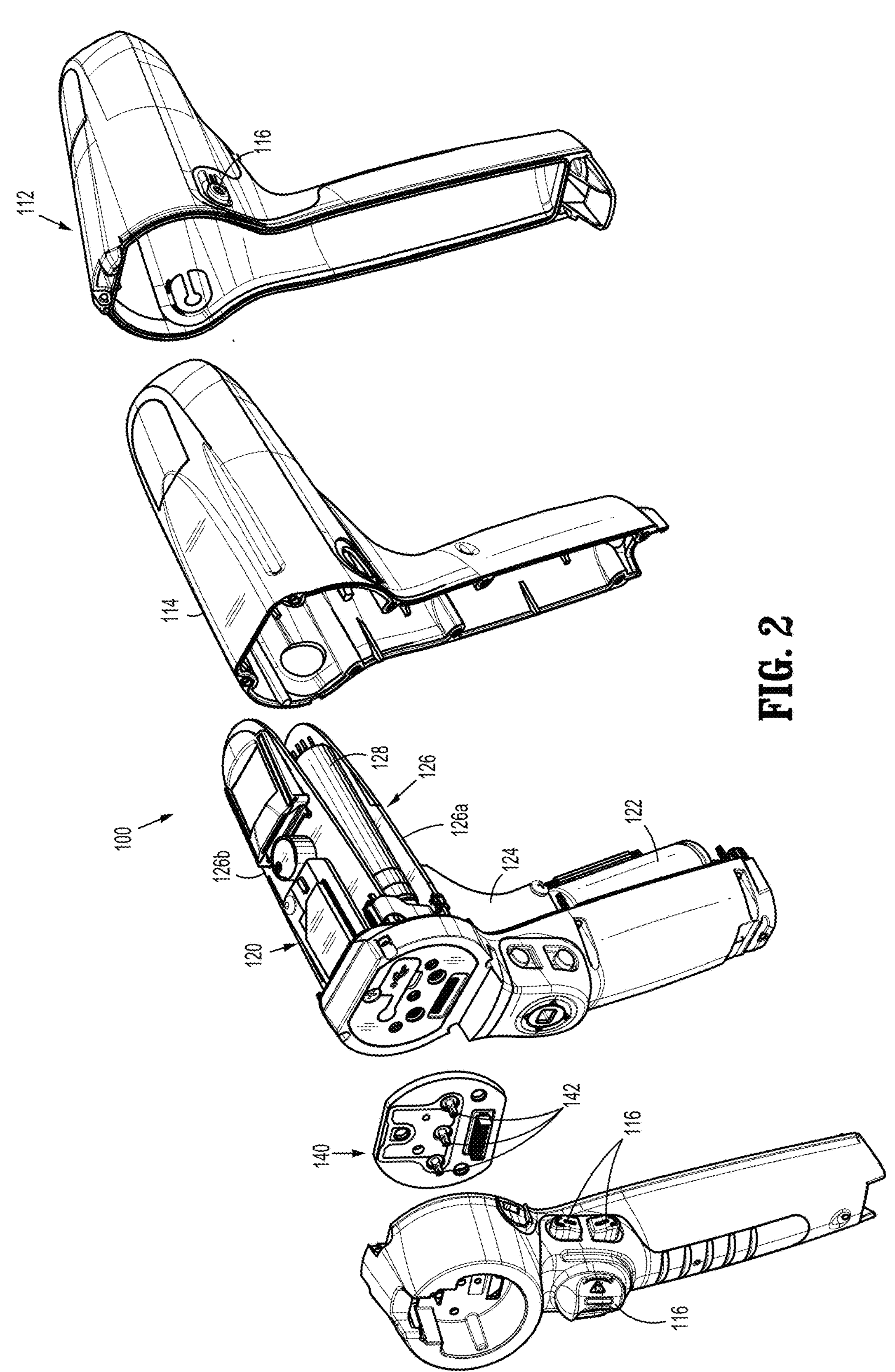
FIG. 2 is a perspective view, with parts separated, of the handle assembly of the surgical device of FIG. 1.

Referring also to FIG. 2 handle assembly 100 generally includes an outer housing shell 112, an inner handle housing 114 disposed within outer housing shell 112, and a power-pack 120 disposed within inner handle housing 114 for powering and controlling the various operations of surgical device 10. A plurality of actuators 116 (e.g., finger-actuated control buttons, knobs, toggles, slides, interfaces, and the like) disposed on outer housing shell 112 communicate with power-pack 120 to enable user-controlled activation of power-pack 120 to perform the various operations of surgical device 10.

Power-pack 120 includes a rechargeable battery 122 configured to supply power to surgical device 10, a battery circuit board 124 (including at least one processor and associated memory), and a controller circuit board 126. Controller circuit board 126 includes a motor controller circuit board **126*a* (including at least one processor and associated memory) and a main controller circuit board 126*b* (including at least one processor and associated memory) operably coupled with one another. Motor controller circuit board 126*a* is operably coupled with battery circuit board 124 enabling communication therebetween and between battery circuit board 124 and main controller circuit board 126*b***.

Power-pack 120 further includes one or more motors 128 each electrically connected to controller circuit board 126 and battery 122. Each motor 128 includes a respective motor shaft (not shown) extending therefrom for transmitting rotative forces and is controlled by a respective motor controller disposed on motor controller circuit board **126*a* to enable independent control of each motor 128. Rotation of each motor shaft by its respective motor 128 functions to drive corresponding components of the adapter assembly 200 in order to perform the various operations of surgical device 10, as detailed below. The motor shaft of each motor 128, more specifically, is configured to cooperate with an output shaft 142 of a plate assembly 140 of handle assembly 100 to provide a rotational output from handle assembly 100 to adapter assembly 200**.

Figure 3:
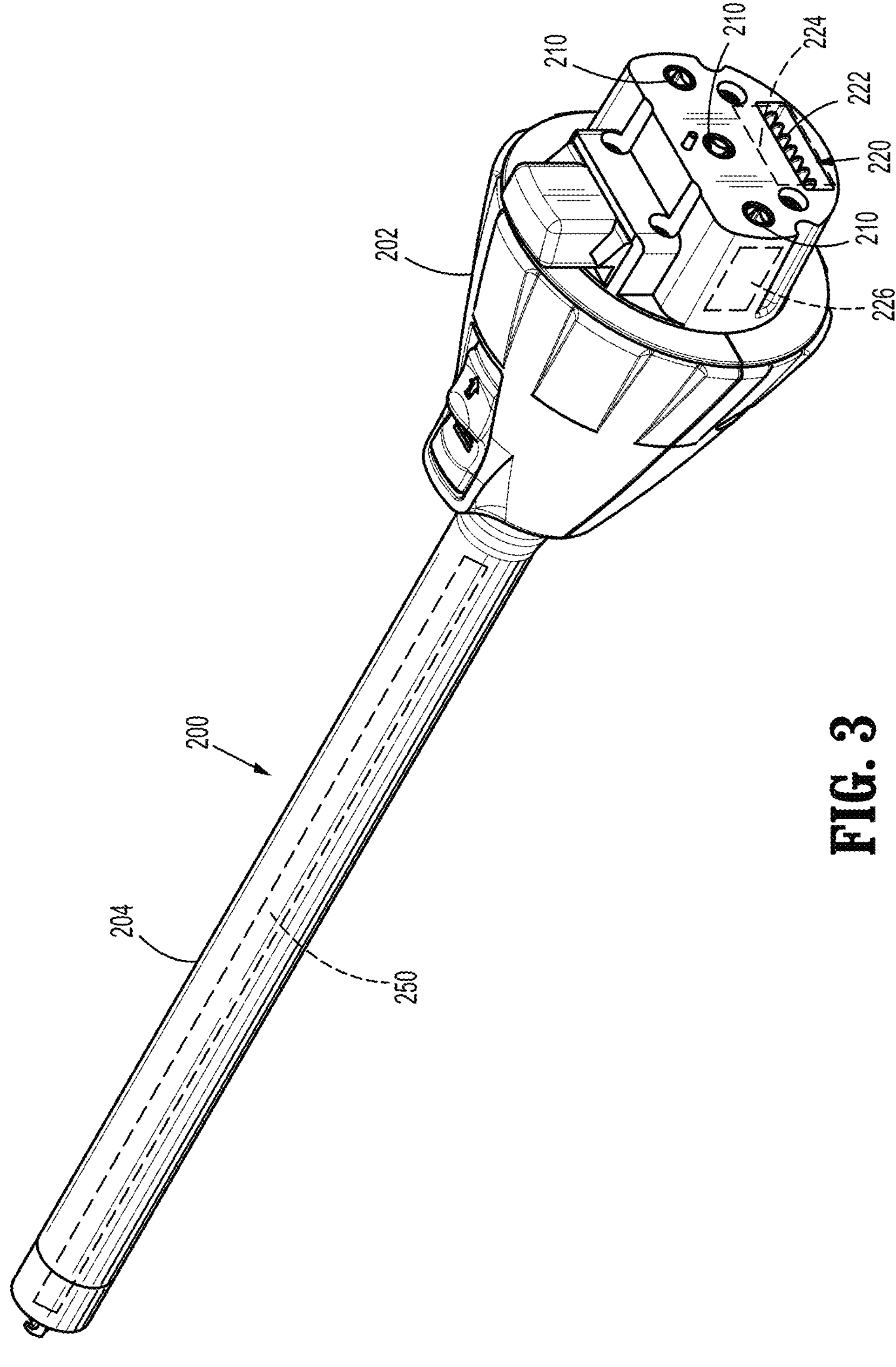
FIG. 3 is a perspective view of the adapter assembly of the surgical device of FIG. 1.

Referring to FIG. 3, in conjunction with FIGS. 1 and 2, adapter assembly 200 includes a connector housing 202 and an outer tube 204 extending distally from connector housing 202. Connector housing 202 is configured for operable connection to handle assembly 100 and the distal end portion of outer tube 204 is configured for operable connection to end effector 300. Adapter assembly 200 further includes one or more rotatable connectors 210 each extending proximally from connector housing 202 and configured to operably couple to a corresponding motor shaft of handle assembly 100 by way of a corresponding output shaft 142 of plate assembly 140 of handle assembly 100 to enable independent rotation of each connector 210 by a respective motor 128, such that rotational force(s) may be selectively transferred from motor(s) 128 of handle assembly 100 to adapter assembly 200. Adapter assembly 200 further includes one or more force/rotation transmitting/converting assemblies (not shown), each extending through connector housing 202 and outer tube 204 and operably coupled to one of the connectors 210. For example, a first force/rotation transmitting/converting assembly may be provided to convert a rotational input from a first of the motors 128 to a first connector 210 into axial translation of an articulation bar (not shown) of adapter assembly 200 to effectuate articulation of end effector 300, a second force/rotation transmitting/converting assembly may be provided to convert a rotational input from a second of the motors 128 to a second connector 210 into rotation of a ring gear (not shown) of adapter assembly 200 to effectuate rotation of adapter assembly 200, and thus, end effector 300, and a third force/rotation transmitting/converting assembly may be provided to convert a rotational input 210 from a third of the motors 128 to a third connector 210 into axial translation of a drive component, e.g., a distal drive member 250 of adapter assembly 200, to effectuate closing, opening, and firing of end effector 300.

An electrical assembly 220 of adapter assembly 200 is supported by connector housing 202 and includes a plurality of electrical contacts 222 extending from a circuit board 224 for electrical connection to handle assembly 100. Electrical assembly 220 also includes a strain gauge 226 electrically connected to circuit board 224, e.g., at least one processor and associated memory thereof, for feedback of closing/firing loads exhibited by adapter assembly 200, e.g., force feedback regarding the distal translation of the distal drive member 250 of adapter assembly 200 to close and fire end effector 300. This force feedback, in turn, is communicated to power-pack 120, e.g., a processor and associated memory of main controller circuit board **126*b* to, in turn, direct the appropriate motor controller of motor controller circuit board 126*a* to set the speed current limit on the appropriate motor 128 to ensure closing and firing forces are maintained within acceptable limits. Circuit board 224 further includes a memory configured to store data relating to adapter assembly 200, e.g., identifying information, life-cycle information, system information, force information, which may likewise be communicated to power-pack 120**.

Figure 4:
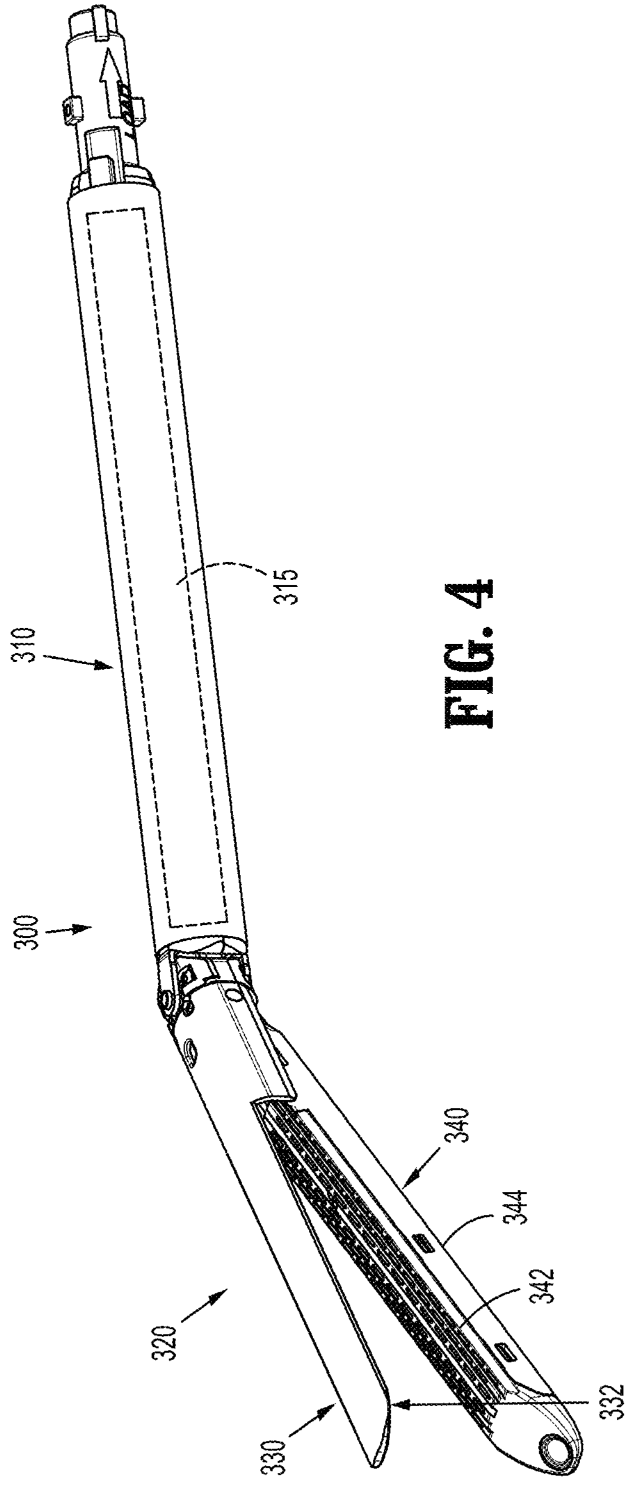
FIG. 4 is a perspective view of the end effector of the surgical device of FIG. 1.

Referring to FIG. 4, end effector 300 is in the form of a linear-stapling, single use loading unit. It should be understood, however, that other types of end effectors may also be used with surgical device 10 of the present disclosure including, for example, end-to-end anastomosis loading units, multi-use loading units, transverse loading units, and curved loading units. The particular end effector 300 utilized with surgical device 10 is recognized by power-pack 120 of handle assembly 100 to enable appropriate operation thereof.

End effector 300 includes a proximal body portion 310 and a tool assembly 320. Proximal body portion 310 is configured to releasably attach to the distal end portion of adapter assembly 200 and tool assembly 320 is pivotally attached to proximal body portion 310. Tool assembly 320 includes an anvil assembly 330 and a cartridge assembly 340. Anvil and cartridge assemblies 330, 340 are pivotal with respect to each other such that tool assembly 320 is movable between an open or unclamped position and a closed or clamped position.

Anvil assembly 330 includes an anvil plate 332 defining a tissue contacting surface (not shown) having a plurality of staple forming pockets (not shown) and a longitudinal slot (not shown) defined therein. Cartridge assembly 340 includes a staple cartridge 342 and a cartridge carrier 344. Staple cartridge 342 defines a tissue contacting surface having staple pockets formed therein for receiving a plurality of staples (not shown) and a longitudinal slot formed in and extending along a substantial length of staple cartridge 342. Cartridge carrier 344 defines an elongated support channel configured to selectively receive staple cartridge 342 therein.

Proximal body portion 310 of end effector 300 includes a drive assembly 315 operably associated with and slidably disposable between anvil and cartridge assemblies 330, 340. Drive assembly 315 includes a drive component, e.g., an elongated drive beam extending to an I-beam including a knife. The I-beam is configured to engage anvil and cartridge assemblies 330, 340 and, upon distal translation relative thereto, pivot anvil and cartridge assemblies 330, 340 relative to one another to close end effector 300 to clamp tissue between the tissue-contacting surfaces of anvil and cartridge assemblies 330, 340. The I-beam is further configured to translate through the longitudinal channels of anvil and cartridge assemblies 330, 340 to drive a sled (not shown) that urges the staples from staple cartridge 342, through clamped tissue, into the staple forming pockets of anvil assembly 330 to fire end effector 300 and form the staples about the clamped tissue. The knife of the I-beam travels through the longitudinal slots defined through anvil and cartridge assemblies 330, 340, to longitudinally cut the clamped and stapled tissue during firing of end effector 300. Drive assembly 315 is operably associated with distal drive member 250 of adapter assembly 200 such that distal translation of distal drive member 250 (effected by a first rotational output received from one of the motors 128 of power-pack 120), is imparted to drive assembly 315 to drive the I-beam to close and fire end effector 300. Proximal translation of distal drive member 250 (effected by a second, opposite rotational output received from one of the motors 128 of power-pack 120), on the other hand, serves to retract drive assembly 315 proximally to return the I-beam to its initial position and open end effector 300 to release the stapled and cut tissue.

For a more detailed discussion of the construction and operation of end effector 300, as illustrated in FIGS. 1 and 4, reference may be made to U.S. Pat. No. 7,819,896, filed on Aug. 31, 2009, entitled "TOOL ASSEMBLY FOR A SURGICAL STAPLING DEVICE," the entire contents of which being incorporated by reference herein.

Referring generally to FIGS. 1-4, as noted above, distal translation (extension) of distal drive member 250 of adapter assembly 200 is imparted to drive assembly 315 of end effector 300 to close and fire end effector 300. As also noted above, power-pack 120 controls one of the motors 128 to provide a rotational output to adapter assembly 200 that, in turn, is converted (via the corresponding force/rotation transmitting/converting assembly of adapter assembly 200) into distal translation of distal drive member 250 and, thus, drives the closure and firing of end effector 300. More specifically, Power-pack 120, e.g., a processor and associated memory of main controller circuit board 126*b*, receives force feedback from strain gauge 226 of adapter assembly 200 (via circuit board 224) to set the speed current limit on the corresponding motor 128 to ensure clamping and firing forces are maintained within acceptable limits. Thus, feedback-based control is effectuated whereby the speed of motor 128 may be increased, decreased, or maintained at different points during a clamping and firing operation based upon the clamping and firing forces encountered, as reported by strain gauge 226.

Once firing is completed and it is desired to retract drive assembly 315 and open end effector 300 to release the stapled and cut tissue, power-pack 120 drives one of the motors 128 to provide a rotational output to adapter assembly 200 that, in turn, is converted (via the corresponding force/rotation transmitting/converting assembly of adapter assembly 200) into proximal translation (retraction) of distal drive member 250. This proximal translation of distal drive member 250, as noted above, drives the retraction of drive assembly 315 and opening of end effector 300. However, neither strain gauge 226 nor any other components of end effector 300 or adapter assembly 200 provides force feedback to power-pack 120 during retraction of drive assembly 315 and, thus, feedback-based control as provided during closing and firing of end effector 300 is not available during retraction.

It has been found that controlling retraction of drive assembly 315 is important to manage retraction forces and thereby prevent system damage or malfunction. On the other hand, it is desirable to minimize retraction time to decrease the lengths of surgical procedures and, thus, the time patients are required to remain under anesthesia. However, as noted above, feedback-based control as provided during closing and firing is not available during retraction.

In order to control retraction to manage retraction forces while minimizing retraction time, the force-feedback from strain gauge 226 used to control closing/firing is utilized during retraction, thus obviating the need for retraction force-feedback. More specifically, a memory associated with a processor of main controller circuit board 126*b* of power-pack 120 (or other suitable memory associated with power-pack 120) is configured to store the force profile (based upon information received from strain gauge 226) and/or motor speed profile (based upon the control of the appropriate motor 128 based upon the force-feedback from strain gauge 226) during closing and firing so that the profile may be utilized to control retraction.

Figure 5A:
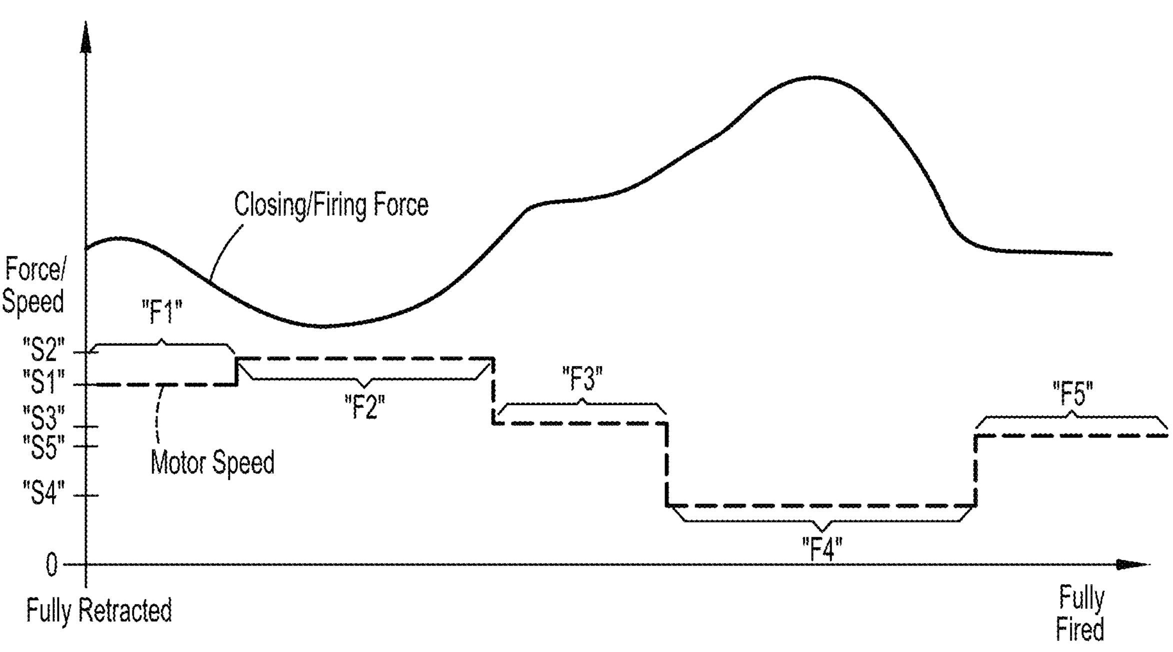
FIG. 5A is a graph illustrating exemplary force and motor speed curves during closing and firing of the surgical device of FIG. 1.

With additional reference to FIG. 5A, sample force and motor speed profiles (for illustrative purposes) for closing/firing are provided. As illustrated, motor 128 is initially driven at a first speed "S1" for an initial, first portion of closing/firing "F1." In response to decreased forces, the speed of the motor 128 is increased to a second speed "S2" during a second portion of closing/firing "F2." A subsequent increase in force causes the motor 128 to be decreased from the second speed "S2" to a third speed "S3" during a third portion of closing/firing "F3." Still further increases in force cause the motor 128 to be decreased to a fourth sped "S4" during a fourth portion "F4" of closing/firing. Finally, a decrease in force causes the motor 128 to increase in speed from the fourth speed "S4" to a fifth speed "S5" during a fifth and final portion of closing/firing "F5."

Figure 5B:
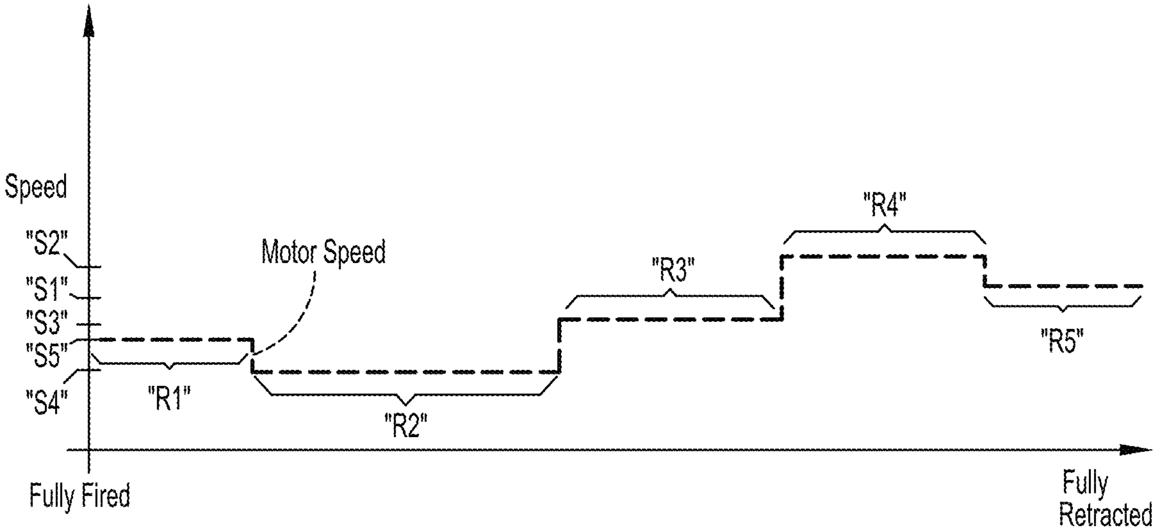
FIG. 5B is a graph illustrating an exemplary motor speed curve during retraction of the surgical device of FIG. 1.

Referring also to FIG. 5B, a sample motor speed profile for retraction based upon the sample force and/or motor speed profiles (see FIG. 5A) for closing/firing is provided. As illustrated in FIG. 5B, motor speed is controlled during retraction to account for the portions of retraction where increased forces are likely to be met and/or where decreased motor speeds are likely to be needed, based upon the closing/firing force profile and/or the closing/firing motor speed profile (see FIG. 5A). As understood, retraction is effected in an opposite direction as closing/firing and, thus, the retraction motor speed profile correlates oppositely to the closing/firing motor speed profile. Similarly, the retraction motor speed profile may correlate oppositely with the closing/firing force profile. More specifically, during an initial, first portion "R1" of retraction, which corresponds to the final, fifth portion "F5" of closing/firing, the motor is set to speed "S5." During a second portion "R2" of retraction, which corresponds to the fourth portion "F4" of closing/firing, the motor is set to speed "S4." During a third portion "R3" of retraction, corresponding to the third portion "F3" of closing/firing, the motor is set to speed "S3." During a fourth portion "R4" of retraction, corresponding to the second portion "F2" of closing/firing, the motor is set to speed "S2." During a final, fifth portion "R5" of retraction, corresponding to the initial, first portion "F1" of closing/firing, the motor is set to speed "S1." Thus, the motor speed is adjusted to account for the portions of retraction where increased forces may be encountered since increased forces were sensed in the corresponding portions of closing/firing, without the need for force feedback during retraction.

Although illustrated as having the motor speeds directly correspond in FIGS. 5A and 5B, the motor speed of the retraction profile need not correspond 1:1 to the motor speed of the closing/firing profile. For example, a scale factor may be introduced to increase or decrease the motor speed during retraction (or portions thereof) as compared to closing/firing; a dampening or strengthening coefficient may be provided to lessen or exaggerate changes in motor speed during retraction (or portions thereof) as compared to closing/firing; upper and/or lower limits in retraction speed may be imposed regardless of the corresponding motor speed during closing firing; and/or other override rules may be implemented. Additionally or alternatively, the firing speed during closing/firing and/or during retraction may be adjusted between two or more incremental settings (e.g., HIGH and LOW; HIGH, MEDIUM, and LOW; etc.) (which may be the same or different between closing/firing and retraction), or may be adjusted continuously during closing/firing and/or during retraction between upper and lower limits (which may be the same or different between closing/firing and retraction).

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A powered electromechanical surgical device, comprising:

- a motor configured to drive extension and retraction of a drive component;
- a sensor configured to sense force exerted on the drive component during extension of the drive component; and
- a controller including a processor and a non-transitory computer-readable storage medium storing instructions that, when executed by the processor, cause the processor to:
  - receive the sensed force from the sensor;
  - control a speed of the motor during extension of the drive component in accordance with the sensed force;
  - generate a speed profile based on the speed of the motor controlled during extension of the drive component from a retracted position to an extended position, wherein the speed profile includes at least one portion corresponding to decelerations in motor speed; and
  - control a speed of the motor during retraction of the drive component from the extended position to the retracted position to replicate the same generated speed profile, which includes the at least one portion corresponding to decelerations in motor speed, in reverse.

2. The powered electromechanical surgical device according to claim 1, wherein the sensed force is an initial sensed force, and wherein the controller further causes the process to:

- during extension of the drive component, upon receiving a second sensed force from the sensor that is higher than the initial sensed, control the speed of the motor by slowing the speed of the motor from an initial speed of the motor to a second speed of the motor; and
- generate the speed profile to include the initial speed of the motor and the second speed of the motor.

3. The powered electromechanical surgical device according to claim 2, wherein the controller further causes the process to:

- during retraction of the drive component, following extension of the drive component, control the speed of the motor to replicate the generated speed profile in reverse, such that the motor operates in reverse, first at the second speed of the motor followed by the initial speed of the motor.

4. The powered electromechanical surgical device according to claim 1, wherein the speed profile includes a plurality of portions corresponding to decelerations in motor speed and at least one portion corresponding to an acceleration in motor speed.

5. The powered electromechanical surgical device according to claim 1, further comprising:

- a handle assembly including the motor and controller disposed therein; and
- an adapter assembly releasably engaged with the handle assembly and including the drive component and sensor disposed therein.

6. The powered electromechanical surgical device according to claim 5, further comprising an end effector releasably engaged with the adapter assembly, wherein extension of the drive component at least one of closes or fires the end effector, and wherein retraction of the drive component opens the end effector.

7. The powered electromechanical surgical device according to claim 1, wherein the sensor is a strain gauge.

8. The powered electromechanical surgical device according to claim 1, wherein the motor provides a rotational output, and wherein the rotational output is converted into translation of the drive component to extend and retract the drive component.

9. A method of controlling a powered electromechanical surgical device, comprising:

- activating a motor to drive extension of a drive component;
- sensing force exerted on the drive component during extension of the drive component;
- controlling a speed of the motor during extension of the drive component in accordance with the sensed force;
- generating a speed profile during extension of the drive component from a retracted position to an extended position, wherein the speed profile includes an initial motor speed and at least one portion corresponding to a second motor speed which is different than the initial motor speed; and
- controlling a speed of the motor during retraction of the drive component from the extended position to the retracted position to replicate the same generated speed profile, which includes the at least one portion corresponding to decelerations in motor speed, in reverse.

10. The method according to claim 9, wherein the sensed force is an initial sensed force, and wherein:

during extension of the drive component, upon receiving a second sensed force that is higher than the initial sensed force, controlling the speed of the motor by slowing the speed of the motor from the initial motor speed to the second motor speed; and generating the speed profile to include the initial motor speed and the second motor speed.

11. The method according to claim 10, wherein:

during retraction of the drive component, following extension of the drive component, controlling the speed of the motor to replicate the generated speed profile in reverse, such that the motor operates in reverse, first at the second motor speed followed by the initial motor speed.

12. The method according to claim 9, wherein the speed profile includes a plurality of portions corresponding to decelerations in motor speed and at least one portion corresponding to an acceleration in motor speed.

13. The method according to claim 9, wherein the speed profile includes a plurality of portions corresponding to progressively stepped decreases in motor speed followed by at least one portion corresponding to a stepped increase in motor speed.

14. The method according to claim 13, wherein:

during retraction of the drive component, following extension of the drive component, controlling the speed of the motor to replicate the generated speed profile in reverse.

15. The method according to claim 14, wherein:

during retraction of the drive component, following extension of the drive component, controlling the speed of the motor to include a plurality of portions of progressively stepped increases in motor speed which correspond to the plurality of portions of progressively stepped decreases in motor speed during extension of the drive component.

16. A method of controlling a powered electromechanical surgical device, comprising:

activating a motor to drive extension of a drive component between a retracted position and an extended position;

during extension of the drive component from the retracted position to the extended position:

sensing a force exerted on the drive component;

controlling a speed of the motor as a function of the sensed force; and generating a speed profile for the motor, wherein the speed profile includes:

an initial motor speed as a function of an initial sensed force; and at least one decelerated motor speed as a function of a corresponding at least one increase in sensed force; and during retraction of the drive component from the extended position to the retracted position:

controlling a retraction speed of the motor, to replicate the same generated speed profile, which includes the at least one portion corresponding to decelerations in motor speed, in reverse.

17. The method according to claim 16, wherein, during extension of the drive component, upon receiving a second sensed force that is higher than the initial sensed force, the method further comprising:

controlling the speed of the motor by slowing the speed of the motor from the initial speed of the motor to a second speed of the motor; and generating the speed profile to include the initial speed of the motor and the second speed of the motor.

18. The method according to claim 17, wherein, during retraction of the drive component, following extension of the drive component, the method further comprising:

controlling the speed of the motor to replicate the generated speed profile in reverse, such that the motor operates in reverse, first at the second speed of the motor followed by the initial speed of the motor.

19. The method according to claim 18, wherein the speed profile includes a plurality of portions corresponding to progressively stepped decreases in motor speed followed by at least one portion corresponding to a stepped increase in motor speed.

20. The method according to claim 19, wherein, during retraction of the drive component, following extension of the drive component, the method further comprising:

controlling the speed of the motor to include a plurality of portions of progressively stepped increases in motor speed which correspond to the plurality of portions of progressively stepped decreases in motor speed during extension of the drive component.

* * * * *